US006979742B1

(12) United States Patent
Torrens Jover et al.

(10) Patent No.: US 6,979,742 B1
(45) Date of Patent: Dec. 27, 2005

(54) PROCESS FOR OBTAINING ENANTIOMERS OF THIENYLAZOLYLALCOXYETHANAMINES

(75) Inventors: Antoni Torrens Jover, Barcelona (ES); Helmut H. Buschmann, Barcelona (ES); Detleff Heller, Rostock (DE); Hans Joachim Drexler, Rostock (DE)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 11/041,639

(22) Filed: Jan. 24, 2005

(30) Foreign Application Priority Data

Dec. 27, 2004 (EP) ................... 04380275

(51) Int. Cl.⁷ .......................... C07D 231/10
(52) U.S. Cl. .................. 548/365.7
(58) Field of Search ................... 548/365.7

(56) References Cited

U.S. PATENT DOCUMENTS 6,743,921 B2    6/2004    Tucker et al.

FOREIGN PATENT DOCUMENTS

| EP | 0 289 380 B1 | 12/1994 |
| WO | WO 99/02500 | 1/1999 |
| WO | WO 99/52525 | 10/1999 |
| WO | WO 2004/011452 A1 | 2/2004 |

OTHER PUBLICATIONS

Burk, Mark J., et al., *A Catalyst for Efficient and Highly Enantioselective Hydrogenation of Aromatic, Heteroaromatic, and α,β-Unsaturated Ketones*, Org. Lett., vol. 2, (2000) 4173-4176.

Cao, Ping, et al., *Ru-BICP-Catalyzed Asymmetric Hydrogenation of Aromatic Ketones*, J. Org. Chem. vol. 64, (1999) 2127-2129.

Chen, Cheng-yi, et al., *Highly Enantioselective Hydrogenation of Aromatic-Heteroaromatic Ketones*, Org. Lett., vol. 5, (2003) 5039-5042.

Noyori, Ryoji, et al., *Asymmetric Catalysis by Architectural and Functional Molecular Engineering: Practical Chemo- and Stereoselective Hydrogenation of Ketones*, Angew. Chem. Int. Ed., vol. 40, (2001) 40-73.

Wu, Jing, et al., *Air-Stable Catalysts for Highly Efficient and Enantioselective Hydrogenation of Aromatic Ketones*, J. Org. Chem. vol. 67, (2002) 7908-7910.

*Primary Examiner*—Kamal A. Saeed
(74) *Attorney, Agent, or Firm*—Steven J. Hultquist; Marianne Fuierer; Intellectual Property/Technology Law

(57) ABSTRACT

A process is described for the preparation of a precursor alcohol of (±)-2-[thienyl(1-methyl-1H-pyrazol-5-yl)methoxy]-N,N-dimethyletanamine, and more generally for thyenylazolylalcoxyethanamines and their enantiomers. The process involves the asymmetric reduction of a prochiral ketone in the presence of a chiral ruthenium (II) catalyst system comprising at least a bidentate phosphorous-containing ligand and a diamine ligand to yield chiral alcohols. The chiral alcohols are further O-alkylated to yield corresponding pharmaceutically active ethanamines.

20 Claims, No Drawings

PROCESS FOR OBTAINING ENANTIOMERS OF THIENYLAZOLYLALCOXYETHANAMINES

CROSS-REFERENCE TO RELATED APPLICATION

The priority of European Patent Application EP04380275.0 filed Dec. 27, 2004 is hereby claimed under the provisions of 35 USC §119.

FIELD OF THE INVENTION

The present invention relates to a new process for the preparation of enantiomerically enriched carbinols substituted simultaneously with pyrazolyl and thienyl heterocycles. The process comprises the enantioselective asymmetric hydrogenation of ketones using chiral catalytic systems to render nonracemic chiral alcohols. More particularly, it relates to a new process for the preparation of the pure enantiomers of intermediate alcohols that are useful intermediates for the preparation of pharmaceutically active thyenylazolylalcoxyethanamines.

BACKGROUND OF THE INVENTION

The compound (±)-2-[phenyl(1-methyl-1H-pyrazol-5-yl)methoxy]-N,N-dimethylethanamine, also referred to as (±)-5-[α-(2-dimethylaminoethoxy)benzyl]-1-methyl-1H-pyrazole, or Cizolirtine, of the formula

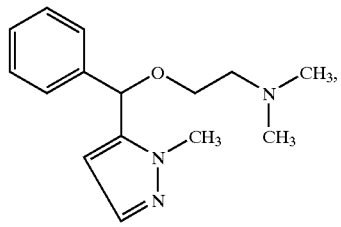

was described in European Patent EP 289 380. This compound is a potent analgesic which is currently in phase II clinical trials. Optical resolution by fractional crystallization with optically active acids has been applied to the Cizolirtine racemate (as described in International Publication WO 99/02500).

A further family of active compounds wherein a thiophene ring is present instead of the phenyl ring has been described in International Publication WO 99/52525. Among them, the compound (±)-2-[thienyl(1-methyl-1H-pyrazol-5-yl)methoxy]-N,N-dimethylethanamine of formula (I)

(I)

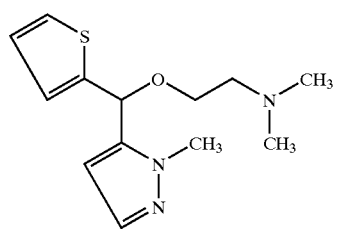

is currently in clinical trials for the treatment of depression. It can be prepared by O-alkylation of the compound of formula II:

(II)

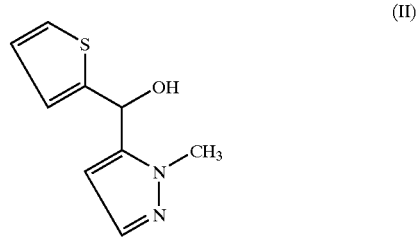

The carbinols such as the one of formula II are key intermediates to reach the compounds described in International Publication WO 99/52525. The pure enantiomers of (+)-I and (−)-I may be prepared by separately O-alkylating the enantiomerically pure intermediates (+)-II and (−)-II. Thus, a synthetic process to the enantiomerically pure/enriched intermediates (+)-II and (−)-II is needed.

The enantioselective reduction of prochiral ketones has been proposed in organic synthesis to obtain secondary alcohols with high enantiomeric purity. Accordingly, a number of strategies for the asymmetric reduction of prochiral ketones to single enantiomer alcohols have been developed [R. Noyori, T. Ohkuma, Angew. Chem. Int. Ed., 2001, 40, 40–73].

A strategy for the enantioselective reduction of aromatic and heteroaromatic prochiral ketones with high ee values includes the use of an optically active diphosphane/Ru/diamine/inorganic base catalyst system. Examples of asymmetric reduction of heteroaromatic ketones are disclosed in International Patent Publication WO 2004/011452 and in P. Cao, X. Zhang, J. Org. Chem. 1999, 64, 2127. Enantioselective hydrogenation of ketonic structures to nonracemic secondary alcohols has also been achieved with a wide range of chiral ruthenium catalyst systems, which can be prepared by different combinations of Ru (II) chiral phosphanes and diamine ligands. The extent of the enantioselectivity obtained with the different ketones depends largely on the nature of the substituents of the prochiral ketone, as shown by the state of the art [see, for instance, Table 2, on p. 53: R. Noyori, T. Ohkuma, Angew. Chem. Int. Ed. 2001, 40, 40–73]. It is also known that heteroaromatic ketones can be enantioselectively hydrogenated to nonracemic secondary alcohols with these chiral ruthenium catalysts systems [C. Chen, R. A. Reamer, J. R. Chilenski, C. J. McWilliams, Org. Lett. 2003 5, 5039].

Nonetheless, it has been found that one specific catalyst or a class of catalysts cannot be used equally well in all hydrogenations. Thus, to attain satisfactory ee values by the enantioselective hydrogenation of prochiral ketones, each hydrogenation problem has to be investigated separately with regard to the substrate, the catalyst and the reaction conditions for finding the optimal conditions to obtain the best results.

SUMMARY OF THE INVENTION

The present invention provides a process for the enantioselective hydrogenation of a thienyl pyrazoyl ketone, which operates particularly well on an industrial scale, is satisfactory as regards yield, conversion and enantiomer excess, and advantageously provides specific enantiomer-enriched alcohols as intermediates for the preparation of (+)- and (−)-thienylazolylalcoxyethanamines.

Surprisingly, the inventors have achieved the enantioselective hydrogenation with a chiral ruthenium (II) catalyst systems of a prochiral ketone with a thienyl and a methyl-pyrazol substituent comprising two nitrogen atoms, with high ee value and high conversion. Investigations carried out by the inventors have shown in a no way foreseeable manner that the prochiral ketone with a thienyl and a methyl-pyrazol substituent provides catalytic enantioselective hydrogenation of said ketone with high enantioselectivity and conversion. This could not have been predicted from the nature of the substrate. We have therefore applied this process to the synthesis of the enantiomerically pure intermediates (+)-II and (−)-II and to a process to obtain 2-[thienyl(1-methyl-1H-pyrazol-5-yl)methoxy]-N,N-dimethylethanamine and in general thienylazolylalcoxyethanamines and their enantiomers. This process is contemplated as operating particularly well on an industrial scale and in a satisfactory manner with regard to enantiomer excess, amount and availability of catalyst, and raw material costs in general.

More specifically, the present invention is directed to a process for the preparation of an enantiomerically enriched compound of formula (II):

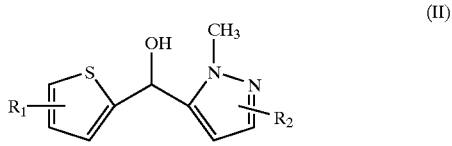

(II)

wherein:
$R_1$ and $R_2$ are independently selected from hydrogen, halogen, lower alkyl or aryl;

In which the process comprises the asymmetric hydrogenation of a prochiral ketone of formula (III)

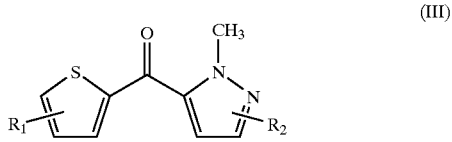

(III)

in the presence of a base and a chiral ruthenium (II) catalyst system comprising at least a bidentate phosphorous-containing ligand and a diamine ligand.

In a preferred embodiment, either of $R_1$ or $R_2$ is H, and in a more preferred embodiment, both are H.

The process of the invention allows the preparation of the known intermediates of formula II, which can be optionally transformed into enantiomerically pure pharmaceutically active compounds.

Other aspects, features and advantages of the invention will be more fully apparent from the ensuing disclosure and appended claims.

DETAILED DESCRIPTION OF THE INVENTION

The process of the invention gives the desired product of formula II with high conversion and enantiomeric excess. This process has the further advantage that the starting materials are not expensive and that the process works under low or normal pressures. Similar hydrogenations are known, as mentioned above, but the present inventors for the first time have applied same to a thienyl pyrazol ketone substrate. Although problems due to the coordination of the pyrazol were expected, we have found on the contrary that the reaction works remarkably well, providing a simple route to the alcohols of formula (II) with high conversion and enantiomeric excess. The process allows the compounds of the above formula (II) to be synthesized directly from the compounds of formula (III), without any further intermediate steps or laborious separation of the isomeric forms.

The product of formula II is especially useful in the preparation of the enantiomers of (±)-2-[thienyl(1-methyl-1H-pyrazol-5-yl)methoxy]-N,N-dimethylethanamine, among others. It will be readily apparent to the person skilled in the art that the process is also applicable to the hydrogenation of other ketones comprising a thienyl substituent and having a different nitrogen-containing heterocycle instead of the methyl pyrazole ring, e.g., methylpyrrole, methyl imidazole or methyl triazole. Different compounds can be obtained depending on the substituents present on the thienyl or N-containing heterocyclic rings.

We will discuss below the different reagents and conditions that are advantageously employed in the process of the invention.

The chiral ruthenium (II) catalyst system used in the process of the present invention is known to the person skilled in the art and is composed of Ruthenium (II) complexes with two different ligands, a bidentate phosphorous-containing ligand and a diamine, in the presence of a base. Such catalyst system components can be provided to the reaction mixture individually to form the reactive catalyst system in situ, or they can be provided as preformed complexes.

The bidentate phosphorous-containing ligand is in general of the biphosphines or biphosphites types, and more preferably it is of the biphosphine type. Illustrative examples of nonracemic chiral diphosphines include 2,2'-bis(diphenylphosphino)-1,1'-binaphtyl (BINAP), TolBINAP and XylBINAP [R. Noyori, T. Ohkuma, Angew. Chem. Int. Ed., 2001, 40, 40–73], 2,2'-bis(diphenylphosphino)-1,1'-dicyclopentane (BICP) [P. Cao, X. Zhang, J. Org. Chem. 1999 64, 2127–2129], 2,2',6,6'-tetramethoxy-4,4'-bis-3,3'-bipyridine (P-Phos), Tol-P-Phos and Xyl-P-Phos [J. Wu, H. Chen, W. Kwok, R. Guo, Z. Zhou, C. Yeung, A. S. C. Chan, J. Org. Chem. 2002, 63, 7908–7910], 4,12-bis(diphenylphosphino)[2.2]paracyclophane (PhanePhos) and Xyl-PhanePhos [M. J. Burk, W. Hems, D. Herzberg, C. Malan, A. Zanotti-Gerosa, Org. Lett. 2000, 2, 4173–4176] and equivalents thereto that are recognized by those skilled in the art.

In one preferred embodiment, the diphosphine ligand comprises a binaphthyl group. More preferably, the diphosphine ligand is selected from the group consisting of the enantiomers of 2,2'-bis(diphenyl-phosphino)-1,1'-binaphtyl (BINAP), TolBINAP and XylBINAP [see R. Noyori, T. Ohkuma, Angew. Chem. Int. Ed., 2001, 40, 40–73].

Suitable diamines include 1,2-diamine species that exhibit a sufficient activity or selectivity in the catalyst under consideration. They can be chiral or non-chiral. Ilustrative examples include any stereoisomers of 1,1-bis(4-methoxyphenyl)-3-methyl-1,2-butanediamine (DAIPEN), 1,2-diphenylethylendiamine (DPEN), 1,2-diaminocyclohexane (DACH) or achiral diamines such as ethylenediamine.

Achiral amines are further discussed in U.S. Pat. No. 6,743,921, the disclosure of which hereby is incorporated herein by reference in its entirety.

The use of enantiomeriacally enriched diamines such as DAIPEN and DPEN has proved particularly advantageous, with DPEN being preferred as regards costs and DAIPEN being preferred as regards higher activity and selectivity.

The bidentate phosphorous-containing ligand together with the diamine and the ruthenium (II) form a complex referred to hereinafter as the ruthenium (II) component of the catalyst system. Examples of preformed complexes of the ruthenium with the diphosphine ligand and the diamine include complexes represented by the formula $RuX_2LA$ wherein X represents a halogen atom or pseudo-halide group, preferably chloride or bromide, L represents the diphosphine ligand and A is the diamine. Suitable examples include $RuCl_2$ [(S)-BINAP][(R,R)-DPEN], $RuCl_2$ [(S)-BINAP] [(S,S)-DPEN], $RuCl_2$ [(R)-BINAP][(R,R)-DPEN], $RuCl_2$ [(R)-BINAP][(S,S)-DPEN], $RuCl_2$ [(R)-BINAP] [(R)-DAIPEN], $RuCl_2$ [(S)-BINAP][(S)-DAIPEN].

Such component is present in catalytic amounts, meaning less than stoichiometric relative to the ketone reactants and as low as possible while ensuring the optimum possible conversion rate. The minimum amount of the ruthenium (II) component of the catalyst system may depend on the activity of the specific catalyst system composition, the reaction temperature, the concentration of the reactants and catalyst system components in the solution, and the maximum time allowed for completion of the reaction. In a typical embodiment, the molar ratio of the ruthenium (II) component of the catalyst to the ketone reactant (s/c) is in the range from about 50 to 20,000, preferably from about 200 to about 20,000, and more preferably from about 10,000 to about 20,000.

Suitable bases include organic bases and inorganic bases, which should not have a negative influence on, for example, the enantiomer purity of the products that are formed. Preferably, the base is selected from the group consisting of hydroxide, $C_1$–$C_5$-alkoxide, bicarbonate, carbonate, di- and tribasic phosphate, borate, fluoride, amine optionally substituted with $C_1$–$C_4$-alkyl or aryl, and silane optionally substituted with $C_1$–$C_3$-alkyl.

In this connection alkali metal alcoholates are advantageous, such as for example t-BuOK, as well as inorganic bases such as for example KOH or $K_2CO_3$. Also used are organic nitrogen bases such as $NEt_3$ and salts as for example $AgCF_3SO_3$. In a more preferred embodiment t-BuOK is used. When the base used is t-BuOK, it is preferably added to the reaction vessel in form of a solution of t-BuOK in t-BuOH.

It has been found that a molar excess of base referred to the ruthenium (II) component of the catalyst system is advantageous. The typical mole ratio of base: ruthenium (II) component of the catalyst system is in a range of from 10:1 and 1:1, more preferably in a range of from about 6:1 to about 4:1. It has been found that both the activity and the selectivity of the hydrogenation vary with the amount of the base. In this respect, the activity of the hydrogenation increases with rising concentration of the base. However, if the concentration of base is too high, then there is a possibility of racemization of the end product, which is not desirable. A ratio in the vicinity of about 6:1 is particularly preferred.

The hydrogenation reaction is conducted in a solvent system that is capable of dissolving the catalyst system and is reaction-inert. The term solvent system is used to indicate that a single solvent or alternatively a mixture of two or more solvents can be used. The term reaction-inert is used to mean that the solvent system does not react unfavourably with the reactants, products, or the catalyst system. The solvent system need not bring about complete solution of the ketone reactant or the chiral alcohol product. The ketone reactant may be incompletely dissolved at the beginning of the reaction or the chiral alcohol product may be incompletely dissolved at the end of the reaction, or both. Representative solvents include alcohol solvents such as methanol, ethanol, n-propanol, 2-propanol, n-butanol, sec-butanol or t-butanol and their mixtures, organic solvents containing heteroatoms such as DMF and ethers such as THF. Preferably the solvent system comprises an alcohol solvent, more preferably methanol, isopropanol, t-butanol and their mixtures. Tert-butanol is a particularly preferred solvent species.

The hydrogenation takes place in a suitable reactor, e.g., a reactor of a type known to the person skilled in the art, such as an autoclave. It is advisable to carry out the hydrogenation under an inert gas atmosphere. Suitable media include, without limitation, nitrogen gas or a noble gas such as argon.

The temperature during the reaction may in principle be chosen arbitrarily by the person skilled in the art, as long as a sufficiently quick and selective reaction is achieved. However, it has to be taken into account that the temperature depends strongly on solvent and that some catalyst systems are instable above 40° C. In typical embodiments, the reaction is suitably conducted at temperature at a temperature in a range of from 10 to 45° C., more preferably in a range of from 20 to 35° C.

The term hydrogenation as used herein refers to reacting the ketone with a source of hydrogen atoms under appropriate conditions so that two hydrogen atoms are added to the carbonyl group of the ketone to produce the hydroxyl group of the chiral alcohol. Preferably the source of hydrogen atoms includes molecular hydrogen ($H_2$). If the hydrogenation is carried out in the presence of molecular hydrogen, the hydrogen pressure in the reaction is preferably low, typically at least about 1.3 atm. More generally, pressure can be in a range of from 0.8 to 100 bar. In a preferred embodiment, the hydrogen pressure is in the range of from 1.3 to 8 bar.

The ketone of formula (III) is known and can be prepared as described for example in International Patent Publication WO99/52525 or by any other suitable method readily apparent to the person skilled in the art. Normally the ketone substrate (III), the catalyst system and the base (if it is a solid) are weighed and introduced in the reactor. Then the solvent is added and stirred to complete dissolution of the catalyst. Thereafter the base, if not a solid, is added. The reactor is brought to adequate temperature and pressure to complete the reaction. Alternatively, the ketone of formula (III) is dissolved in an appropriate solvent, then the constituents of the catalyst system or the catalyst in preformed form are added, and then the hydrogenation is performed at appropriate temperature and suitable hydrogen pressure.

The ketone concentration ranges from about 0.025 to 0.1 mol/l, and preferably from about 0.05 to about 0.1 mol/l. In general the reaction is allowed to continue until complete conversion of the ketone is achieved. Reaction time in a range of from 1 to 110 hours is generally sufficient, although shorter times are preferred in terms of economy of the process.

The advantages associated with the invention are numerous. The process according to the invention provides a simple means of access to isomers which were previously relatively difficult to obtain, and also allows this to be done on a large industrial scale with excellent productivity. The process according to the invention makes it possible to prepare the desired product not only in high yields but also with very high enantioselectivity. No additional purification steps are needed, and the products may be further processed directly just as they occur.

Conversions of 100% of the ketone are achieved by the process of the present invention. The enantiomeric proportions achieved by the process of the invention are above 90 ee %. Since the constituents of the catalyst (diamine, ruthenium (II) and bidentate phosphorous containg ligand) may be used in several diasteromeric and enantiomeric forms and the complex in each case may therefore be present in so-called matched or mismatched configurations with regard to the chiral ketone, the person skilled in the art is able to appropriately verify which pair works most suitably as regards selectivity.

In one preferred embodiment, the process of the invention is directed to the synthesis of each of the following alcohols of formula II with the highest possible enantiomeric purity:

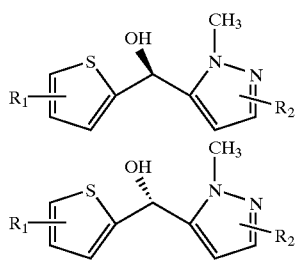

wherein $R_1$ and $R_2$ are as defined above.

It will be readily apparent to the person skilled in the art that the process is also applicable for the hydrogenation of other thienyl ketones having a different nitrogen-containing heterocycle instead of the pyrazole ring, such as pyrrole, imidazole or triazole.

Thus, in another aspect, the invention relates to a process as defined above which further comprises the step of O-alkylation of an enantiomerically enriched compound of formula (II) to yield the desired enantiomer of a pharmaceutically active compound as described in International Patent Publication WO 99/52525. To this end the compound of formula (II) is treated with an amine of formula

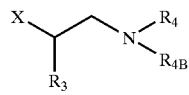

wherein
X is a suitable leaving group such as halogen, more preferably chlorine, bromine or iodine; a reactive esterified hydroxyl, for example arylsulfonyloxy such as phenylsulfonyloxy; tosyloxy; mesyloxy; $C_{1-4}$ alkyl sulfonyloxy, for example methanesulfonyloxy; arylphosphoryloxy, for example diphenylphosphoryloxy, dibenzylphosphoryloxy or a $C_{1-4}$ alkyl phosphoryloxy, for example dimethylphosphoryloxy, and $R_3$, $R_4$ and $R_{4B}$ are independently selected from H and a lower alkyl.

Preferably $R_3$ is hydrogen.

Preferably $R_4$ and $R_{4B}$ are independently selected from H and methyl.

In one embodiment both $R_4$ and $R_{4B}$ are methyl.

A particularly preferred amine for the step of O-alkylation is X—$CH_2$-$CH_2$N(Me)$_2$. More preferably X is chlorine.

The O-alkylation has been described in International Patent Publication WO 99/52525, the disclosure of which hereby is incorporated herein in its entirety.

The alkylation preferably is carried out directly in the same reaction medium resulting from the process of the invention, without further purification of the carbinol. In general, the O-alkylation is carried out in conditions of phase transfer, using for example 2-chloro-N,N,-dimethylethylamine (other leaving groups instead of chloro are possible), an alkaline aqueous solution such as NaOH or KOH, in the presence of a catalyst such as a quaternary ammonium salt. Accordingly, the same solvent as the one used in the process of the invention is used, such as toluene. In these conditions we have the further advantage that the impurities, e.g., any remaining zinc salts, are also eliminated through the aqueous phase.

The resulting product of formula I is enantiomerically enriched, and it can be further purified using polar organic solvents. Further, a pharmaceutically acceptable salt of the obtained compound can be formed. For example, the citrate salt can be prepared by dissolving the amine of formula I in ethanol and treating the solution with citric acid monohydrate. The preparation of other salts will be readily apparent to the person skilled in the art.

The following examples will further illustrate the invention, and are not to be interpreted as limiting, as regards the scope of the invention.

EXAMPLES

General Methods and Materials.
a) Reactions in autoclave

The substrate, and the components of the chiral ruthenium (II) catalyst system used in the process of the present invention, bidentate phosphorous-containing ligand, amine and base (if the base is a solid) are weighed (it is not necessary that anaerobic conditions be used in such step) in a Schlenk flask. With larger quantities of substrate (more than 1.5 mmol), the substrate is filled directly into the autoclave. The Schlenk flask is securated and the solvent (stock solution) is added under anaerobic conditions. The formed suspension is stirred until the dissolution of the chiral ruthenium (II) catalyst system has been completed (~5 min). Then the base solution is added with a securated Hamilton glass syringe and stirred again for 5 minutes if it was not already added as a solid at the beginning. Afterwards the solution is transferred into the securated autoclave standing under vacuum (via capillary and argon pressure). The reaction solution is then heated to the desired temperature. The desired hydrogen pressure is adjusted.

b) Reactions at normal pressure

The substrate, and the components of the chiral ruthenium (II) catalyst system used in the process of the present invention, bidentate phosphorous-containing ligand, amine and base (if the base is a solid) are weighed (it is not necessary to use anaerobic conditions for such step) and provided in an adjustable temperature two neck reaction vessel. This is connected to a dropping funnel containing the solvent (stock solution, anaerobic conditions) and the normal pressure registration equipment. Afterwards this complete system is carefully securated. The solution in the dropping funnel is added to the solids in the reaction vessel and the base solution is added to the suspension. Then the argon is replaced with hydrogen (3×securation with hydrogen). Normal pressure is adjusted by deflating the overpressure over a bubble counter and the measurement is started.

Example 1

Preparation of the enantiomerically enriched thienyl 1-methylpirazoyl carbinol

TABLE 1

Preparation of the enantiomerically enriched thienyl 1-methylpirazoyl carbinol (variation of standard condition*)

| entry | s/c | Diamine | solvent | pressure temperature | time (conversion) | enantiomeric excess |
|---|---|---|---|---|---|---|
| 1 | 50 | R-DAIPEN | 20 ml isopropanol | 8 bar 25° C. | 1.5 h (100%) | 90 ee % |
| 2 | 50 | R-DPEN | 20 ml isopropanol | 8 bar 25° C. | 1.5 h (100%) | 86 ee % |
| 3 | 50 | R,R-DACH | 20 ml isopropanol | 8 bar 25° C. | 4 h (100%) | 83 ee % |
| 4 | 50 | R-DPEN | 20 ml isopropanol | 3 bar 25° C. | 3 h (100%) | 85 ee % |
| 5 | 50 | R-DPEN | 20 ml isopropanol | 20 bar 25° C. | 1 h (100%) | 85 ee % |
| 6 | 50 | R-DPEN | 20 ml isopropanol | 80 bar 25° C. | 0.5 h (100%) | 86 ee % |
| 7 | 100 | R-DPEN | 20 ml isopropanol | 8 bar 30° C. | 0.5 h (100%) | 86 ee % |
| 8 | 100 | R,R-DPEN | 20 ml t-butanol | 8 bar 30° C. | 2 h (100%) | 86 ee % |
| 9 | 100 | R,R-DPEN | 19 ml t-butanol 1 ml isopropanol | 8 bar 30° C. | 0.4 h (100%) | 86 ee % |
| 10 | 125 | R,R-DPEN | 19 ml t-butanol 1 ml isopropanol | 8 bar 30° C. | 0.6 h (100%) | 86 ee % |
| 11 | 500 | R,R-DPEN | 19 ml t-butanol 1 ml isopropanol | 8 bar 30° C. | 3.5 h (100%) | 87 ee % |
| 12 | 100 | R,R-DPEN | 20 ml isopropanol | 1 bar 25° C. | 4 h (97%) | 84 ee % |
| 13 | 100 | R,R-DPEN | 20 ml t-butanol | 1 bar 30° C. | 4.5 h (100%) | 88 ee % |
| 14 | 100 | R,R-DPEN | 19 ml t-butanol 1 ml isopropanol | 1 bar 25° C. | 4.5 h (100%) | 88 ee % |

*Standard conditions: 0.01 mmol R,R-Ru(BINAP); 0.01 mol diamine; 0.5 to 5 mmol ketone; 0.06 mmol t-BuOK; 20 ml solvent; 1–100 bar $H_2$; 10–45° C.

Entry 1, 2 and 3
according to method a)

The compound was prepared from 0.5 mmol thienyl 1-methylpyrazoyl ketone
0.01 mmol R-Ru(BINAP); 0.01 mmol R-DAIPEN, R,R-DPEN or R,R-DACH;
0.06 mmol t-BuOK (60 µl, t-BuOK 1.0 M solution in t-BuOH);
20 ml isopropanol,
at 25° C. and 8 bar $H_2$.

Conversion:
100% after 1.5 hr with 90% ee for R-DAIPEN,
100% after 1.5 hr with 86% ee for R,R-DPEN and
100% after 4 hr with 83% ee for R,R-DACH.

Entry 4, 5 and 6
according to method a)

The compound was prepared from 0.5 mmol thienyl 1-methylpyrazoyl ketone
0.01 mmol R-Ru(BINAP); 0.01 mmol R,R-DPEN;
0.06 mmol t-BuOK (60 µl, t-BuOK 1.0 M solution in t-BuOH);
20 ml isopropanol,
at 25° C. and 3, 20 or 80 bar $H_2$.

Conversion:
100% after 3 hr with 85% ee for 3 bar,
100% after 1 hr with 85% ee for 20 bar and
100% after 0.5 hr with 86% ee for 80 bar.

Entry 7, 8 and 9
according to method a)

The compound was prepared from 1 mmol thienyl 1-methylpyrazoyl ketone
0.01 mmol R-Ru(BINAP); 0.01 mmol R,R-DPEN;
0.06 mmol t-BuOK (60 µl, t-BuOK 1.0 M solution in t-BuOH);
20 ml isopropanol, 20 ml t-butanol or 19 ml t-butanol and 1 ml isopropanol;
at 30° C. and 8 bar $H_2$.

Conversion:
100% after 0.5 hr with 86% ee for 20 ml isopropanol,
100% after 2 hr with 86% ee for 20 ml t-butanol and
100% after 0.4 hr with 86% ee for 19 ml t-butanol and 1 ml isopropanol.

Entry 10 and 11
according to method a)

The compound was prepared from 1.25 mmol or 5 mmol thienyl 1-methylpyrazoyl ketone
0.01 mmol R-Ru(BINAP); 0.01 mmol R,R-DPEN;
0.06 mmol t-BuOK (60 µl, t-BuOK 1.0 M solution in t-BuOH);

19 ml t-butanol and 1 ml isopropanol;
at 30° C. and 8 bar H$_2$.

Conversion:
100% after 0.6 hr with 86% ee for 1.25 mmol ketone and 100% after 3.5 hr with 87% ee for 5 mmol ketone.

Entry 12, 13 and 14
according to method b)

The compound was prepared from 1 mmol thienyl 1-methylpyrazoyl ketone
0.01 mmol R-Ru(BINAP); 0.01 mmol R,R-DPEN;
0.06 mmol t-BuOK (60 µl, t-BuOK 1.0 M solution in t-BuOH);
20 ml isopropanol, 20 ml t-butanol or 19 ml t-butanol and 1 ml isopropanol;
at 25° C. (30° C. for pure t-butanol) and 1 bar H$_2$.

Conversion:
97% after 4 hr with 84% ee for 20 ml isopropanol,
100% after 4.5 hr with 88% ee for 20 ml t-butanol and
100% after 4.5 hr with 88% ee for 19 ml t-butanol and 1 ml isopropanol.

The best results concerning the selectivity where obtained with DAIPEN entry 1 and concerning the activity with the 19 to 1 mixture of t-butanol and isopropanol at 8 bar and 30° C., see entry 11.

What is claimed is:

1. A process for the preparation of an enantiomerically enriched compound of formula (II):

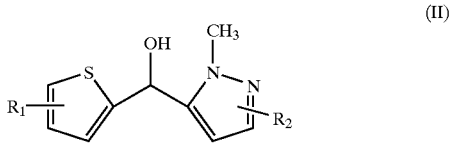

(II)

wherein:
R$_1$ and R$_2$ are independently selected from hydrogen, halogen, lower alkyl and aryl; comprising asymmetric hydrogenation of a prochiral ketone of formula (III)

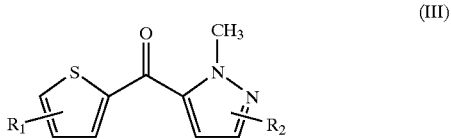

(III)

in the presence of a base and a chiral ruthenium (II) catalyst system comprising at least a bidentate phosphorous-containing ligand and a diamine ligand.

2. A process according to claim 1, wherein the bidentate phosphorous-containing ligand is a bisphosphine ligand comprising a binaphthyl group.

3. A process according to claim 1, wherein the bidentate phosphorus-containing ligand comprises a ligand selected from the group consisting of stereoisomers of 2,2'-bis(diphenyl-phosphino)-1,1'-binaphtyl (BINAP), TolBINAP and XylBINAP.

4. A process according to claim 1 wherein the diamine comprises an enantiomerically-enriched 1,2 diamine.

5. A process according to claim 1, wherein the diamine is selected from the group consisting of 1,1-bis(4-methoxyphenyl)-3-methyl-1,2-butanediamine (DAIPEN), 1,2-diphenyl-ethylendiamine (DPEN) and 1,2-diaminocyclohexane (DACH).

6. A process according to claim 1, wherein the diamine is DAIPEN.

7. A process according to claim 1, wherein the base is selected from the group consisting of alkali metal alcoholates.

8. A process according to claim 1, wherein the base is t-butanolate.

9. A process according to claim 1, wherein the base is selected from the group consisting of t-BuOK, KOH, K$_2$CO$_3$, NEt$_3$ and AgCF$_3$SO$_3$.

10. A process according to claim 1, wherein the base is t-BuOK.

11. A process according to claim 1 wherein the mole ratio of base:ruthenium (II) component of the catalyst system is in a range of from 10:1 to 1:1.

12. A process according to claim 1 wherein the mole ratio of base:ruthenium (II) component of the catalyst system is in a range of from 6:1 to 2:1.

13. A process according to claim 1 wherein the mole ratio of base:ruthenium (II) component of the catalyst system is in a range of from 6:1 and 4:1.

14. A process according to claim 1, wherein the solvent comprises an alcohol.

15. A process according to claim 1, wherein the solvent is selected from the group consisting of methanol, isopropanol, t-butanol and their mixtures.

16. A process according to claim 1, wherein the solvent is t-butanol.

17. A process according to claim 1, which further comprises an O-alkylation of the enantiomerically enriched compound of formula II.

18. A process according to claim 17, wherein the O-alkylation is carried out without an intermediate separation or purification step.

19. A process according to claim 1, wherein either of R$_1$ or R$_2$ is H.

20. A process according to claim 1, wherein both of R$_1$ and R$_2$ are H.

* * * * *

UNITED STATES PATENT AND TRADEMARK OFFICE
CERTIFICATE OF CORRECTION

| | | |
|---|---|---|
| PATENT NO. | : 6,979,742 B1 | |
| APPLICATION NO. | : 11/041639 | |
| DATED | : December 27, 2005 | |
| INVENTOR(S) | : Antoni Torrens Jover et al. | |

It is certified that error appears in the above-identified patent and that said Letters Patent is hereby corrected as shown below:

Column 4, line 22, "methylpyrrole" should be -- methyl pyrrole --

Signed and Sealed this

Eleventh Day of July, 2006

JON W. DUDAS
*Director of the United States Patent and Trademark Office*